United States Patent [19]

Perrotta et al.

[11] Patent Number: 6,153,747
[45] Date of Patent: Nov. 28, 2000

[54] PROCESS FOR THE PREPARATION OF 2-HALOMETHYL-PENEMS AND THEIR USE FOR THE PREPARATION OF ANTIBACTERIAL PENEMS

[75] Inventors: Enzo Perrotta; Maria Altamura, both of Florence, Italy

[73] Assignees: A. Menarini Industrie Farmaceutiche Riunite S.r.l., Florence; Istituto Luso Farmaco D'Italia S.p.A., Milan, both of Italy

[21] Appl. No.: 09/130,264

[22] Filed: Aug. 6, 1998

[30] Foreign Application Priority Data

Feb. 27, 1996 [IT] Italy .................. FI96A0033

[51] Int. Cl.[7] ............ C07D 499/887; C07D 205/09
[52] U.S. Cl. ....................... 540/210; 540/357
[58] Field of Search ................ 540/357, 310

[56] References Cited

U.S. PATENT DOCUMENTS 4,631,150 12/1986 Battistini ............... 540/310
4,794,109 12/1988 Lang ................... 540/310

FOREIGN PATENT DOCUMENTS

| 115969 | 8/1984 | European Pat. Off. . |
| 2449690 | 2/1980 | France . |
| 2550533 | 8/1994 | France . |
| 2118181 | 10/1983 | United Kingdom . |
| 92/20689 | 10/1992 | WIPO . |

OTHER PUBLICATIONS

Wise, Antimicrobial Newsletter 7(10), 73, Oct. 1990.
Pentassuglia, J. Antibiotics 48, 399, May 1995.
Altamura, J. Org. Chem 58, 272, Jan. 1993.
Arndt, Berichte 63, 2390, 1930.

*Primary Examiner*—Mark L. Berch
*Attorney, Agent, or Firm*—Hedman, Gibson & Costigan, P.C.

[57] ABSTRACT

Process for the preparation of 2-halomethyl-penems (I) comprising (a) reacting an acetoxy-(protected hydroxyethyl)-2-azetidinone (III) with a 2-halothioacetic acid to form a 3-haloacetylthioazetidinone (V), (b) reacting (V) with oxalyl chloride to give an intermediate (VII), acylated on the beta-lactamic nitrogen, and (c) cyclizing (VII) in the presence of an organic phosphate or phosphonite to produce the corresponding 2-halomethyl-penem (I).

8 Claims, No Drawings

PROCESS FOR THE PREPARATION OF 2-HALOMETHYL-PENEMS AND THEIR USE FOR THE PREPARATION OF ANTIBACTERIAL PENEMS

The present application is the national stage filing of and claims priority to International Application No. PCT/EP97/00783, filed Feb. 19, 1997 and Italian Application Serial. No. FI96A000033.

FIELD OF THE INVENTION

The present invention refers to a process for the preparation of 2-halomethyl-penems (in particular 2-chloromethyl-penems) useful for the preparation of antibacterial penems.

STATE OF THE ART

It is known that penem-derivatives are compounds endowed with a wide activity spectrum against bacteria [see for example Wise R. "The Carbapenem and Penem Antibiotics—A Brief Review"—Antimicrob. Newsl. 7, 73–80 (1990)].

It is also known that 2-halomethyl-penems of formula (I) (in particular 2-chloromethyl-penems) are useful intermediates for the preparation of antibacterial penems [G. Pentassuglia et al. J of Antibiotics Vol. 48, 399–407 (1995)]. The processes for the preparation 2-halomethyl-penems (I) known up to now [see for example Altamura M. et al. J. Org. Chem. 1993, 58, 272–274] comprise a step involving the corresponding 2-hydroxymethyl-penem (II):

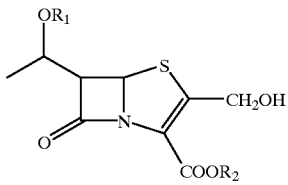

(II)

wherein $R_1$ and $R_2$ are as hereinafter defined.

The preparation of compound (II) requires a long serie of complicated steps, giving low yields and involving the use of protecting groups and expensive reagents, which are not suitable for industrial production.

Moreover, the synthesis of (II) requires many chromatographic separations for the purification of the obtained compounds since their use as crude products in the following acid or basic reaction conditions is not suitable because of their low stability.

SUMMARY OF THE INVENTION

The present invention refers to a process for the preparation of 2-halomethyl-penems (in particular 2-chloromethyl-penems) of formula (I)

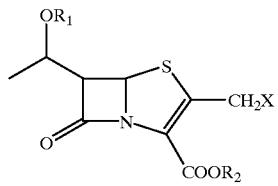

(I)

wherein $R_1$ is a protecting group for the alcoholic hydroxyl, $R_2$ is a protecting group for the carboxyl and X is an halogen, in particular chorine, comprising, as intermediate step, the formation of the corresponding 2-haloacetylthio-azetidone.

DETAILED DESCRIPTION OF THE INVENTION

It has now been found, and it is an object of the present invention, a process which produces the 2-halomethyl-penems (I) (in particular 2-chloromethyl-penems) with only three steps using as starting product a product which is easily commercially available. The synthesis path, described in the Flow Chart hereinafter, permits to obtain the compounds of formula (I) without requiring intermediate steps involving protection and deprotection and using, for the production of the final product, all the carbon atoms added during the synthesis. Moreover the process object of the present invention does not involve the complicated methods of separation or purification of the intermediates and therefore it provides the compounds of formula (I) with high yields. Moreover the reaction conditions provides the compounds (I) with high stereoselectivity since during the process according to the invention only the desired optical isomer is formed. The 2-halomethyl-penems of formula (I) can be directly transformed, after removing the protective groups, into the desired final products.

As reported in the Flow Chart hereinafter the process according to the invention comprises the reaction between a compound of formula (III), (3R,4R)-4-acetoxy-3-[$R_1$O-ethyl]-2-azetidinone, wherein $R_1$ is as defined above, and a 2-halothioacetic acid (IV) wherein X is an halogen, prepared, for example, as described in: Arndt, Bekir Berichte, 63B, 2390 (1930). The reaction is carried out in an organic non-protic solvent, preferably dioxane, tetrahydrofuran, chloroform at a temperature of −10° C.−+40° C., in the presence of an organic base, as triethylamine or diisopropylethylamine, and of a Lewis acid, as zinc iodide, zinc bromide, zinc chloride, aluminium chloride. The 2-haloacetylthio azetidone (V) can be reacted, without further purification, with an oxallyl chloride ester (VI).

Such reaction is performed in a non-protic organic solvent, preferably dioxane, tetrahydrofuran, toluene, chloroform, at a temperature of −60° C.−+20° C., preferably −20° C.−+10° C., in the presence of an organic base, as triethylamine or diisopropylethylamine.

The intermediate (VII), acylated on the β-lactamic nitrogen, is cyclized into the corresponding 2-halomethyl-penem (I), under the action of an organic phosphite, as triethylphosphite or trimethylphosphite, or phosphonite, as dimethoxymethylphosphine, in an organic solvent as toluene, xylene, chloroform, methylene chloride, at a temperature of 20° C.−140° C., for a time of 1–120 h.

The reaction mixture containing the crude 2-halomethyl-penem (I) can be used directly, without further purification, to obtain the desired penem-derivatives (for example as described in U.S. Pat. No. 4,794,109).

In particular the present invention refers to a process for the preparation of 2-chloromethyl-penems [compounds of formula (I) wherein X=Cl, $R_1$ and $R_2$ are as above defined].

According to the invention the group $R_1$, protecting the alcoholic hydroxyl-group is preferably a tri-$C_{1-6}$alkyl-silyl (in particular tert-butyl-dimethyl-silyl and trimethylsilyl), allyloxycarbonyl, p-nitrobenzyloxycarbonyl; while the group $R_2$, protecting the carboxyl-group, is preferably allyl, benzyl (possibly substituted with a methoxy- or nitro-group), $CH_2OCO(O)_mR_4$ wherein $R_4$ is a $C_{1-6}$alkyl-group and m is 0 or 1.

Halogen according to the present invention is: chlorine, bromine, iodine, in particular chlorine.

The following examples are reported to better illustrate the invention.

EXAMPLE 1

(3S,4R)-3-[(R)-tert-butyldimethylsilyloxy)ethyl]-4-(2-chloroacetylthio)-2-azetidone 83.3 g (0.261 moles) of zinc iodide are added, at 20° C. under nitrogen, in a solution of 50 g (0.174 moles) of (3R,4R)-4-acetoxy-3-[(R)-tertbutyldimethylsilyloxy)ethyl]-2-azetidone; after 15 minutes 38.3 g (0.346 moles) of 2-chloroacetic acid are added. The mixture is cooled down to 12° C. and thereafter, in 1 h, a solution of 26.5 ml (0.190 moles) of triethylamine in dioxane (50 ml) is added therein. The mixture is stirred for 2 h at the same temperature. 5.0 ml (0.036 moles) of triethylamine are added and the mixture stirred for 30 minutes.

The solution is poured in a cold solution of $NaHSO_3$ 3% and extracted with ethylacetate. The organic phase is washed with solutions of $NaHSO_3$ 3%, $NaHCO_3$ 5%, water, NaCl 10% and dried on anhydrous $Na_2SO_4$. By evaporating the solvent, under vacuum, a yellow-brownish is obtained. Ethylether is added, the solvent is evaporated and a pale-yellow solid is obtained. Yield: 57 g (97%).

1H NMR (200 MHz) ($CDCl_3$): d 0.07 (3H, s), 0.08 (3H, s), 0.88 (9H, s), 1.21 (3H, d, J=6.3 Hz), 3.23 (1H, dd, J=2.3, 4.0 Hz), 4.22 (2H, s), 4.27 (1H, qd, J=3.7, 6.3 Hz), 5.32 (1H, d, J=2.3 Hz), 6.4 (1H, br s). $^{13}C$ NMR (50 MHz) ($CDCl_3$): d −4.3, −5.1, 17.9, 22.3, 25.7, 48.0, 52.4, 64.6, 65.4, 166.1, 194.8. MS TS (m/z): $(M+H)^+$ 338, $(M+NH_4)^+$ 355.

EXAMPLE 2

(3S,4R)-1-(allyloxyoxalyl)-3-[(R)-tert-butyldimethyl-silyloxy)-ethyl]-4-(2-chloroacetylthio)-2-azetidone To a solution of 57 g (0.169 moles) of (3S,4R)-3-[(R)-tert-butyldimethylsilyloxy)ethyl]-4-(2-chloro-acetylthio)-2-azetidone in anhydrous tetrahydrofuran (500 ml) 42.3 ml (0.338 moles) of allyloxyoxalyl chloride are added, at 0°–3° C., under nitrogen. The mixture is stirred for some minutes and then a solution of 43.4 ml (0.254 moles) of diisopropylethylamine in tetrahydrofuran (40 ml) is added, drop by drop, in 45 minutes. The mixture is stirred 30 minutes at the same temperature. 15 ml (0.087 moles) of diisopropylethylamine are added, the solution stirred 30 minutes and filtered.

The filtrate is poured in a cold solution of $NaHCO_3$ 5% and extracted with n-hexane, washing with the same solvent the solid remained on the filter. The organic phases are pooled together, washed with water and NaCl 10% and dried on anhydrous $Na_2SO_4$. By evaporating the solvent a brownish oil is obtained which is used in the following step without further purification. Yeld: 73.0 g (96%).

$^1H$ NMR (200 MHz) ($CDCl_3$): d −0.04 (3H, s), −0.09 (3H, s), 0.85 (9H, s), 1.24 (3H, d, J=6.3 Hz), 3.52 (1H, t, J=3 Hz), 4.26 (2H, s), 4.38 (1H, qd, J=3, 6.3 Hz), 4.70–4.82 (2H, m), 5.22–5.46 (2H, m), 5.80–6.06 (1H, m), 5.97 (1H, d, J=3 Hz). $^{13}C$ NMR (50 MHz) ($CDCl_3$): d −5.2, −4.3, 17.8, 21.7, 25.6, 47.9, 53.8, 64.7, 66.3, 67.4, 120.1, 130.5, 154.5, 159.0, 162.9, 190.7. MS TS (m/z): $(M+NH_4)^+$ 467.

EXAMPLE 3

Allyl (5R,6S)-2-chloromethyl-6-((R)-1-tert-butyldimethylsilyloxy-ethyl)-penem-3-carboxylate To a solution of 73 g (0.162 moles) of (3S,4R)-1-(allyloxyoxalyl)-3-[(R)-tert-butyldimethyl-silyloxy)-ethyl]-4-(2-chloroacetylthio)-2-azetidone in 730 ml toluene 59 g (0.356 moles) of triethylphosphite are added. The solution is refluxed for 3 h. The solution is cooled and concentrated under vacuum giving, after column chromatography (silica gel; cyclohexane/ethylacetate 3:1 v/v), the desired allyl (5R,6S)-2-chloromethyl-6-((R)-1-tert-butyldimethylsilyloxy-ethyl)-penem-3-carboxylate as a yellow oil. Yeld 82%.

HPLC: 1) Column: Hypersil 5 ODS 5 mm $C_{18}$, 4.6×250 mm; mobile phase: water/acetonitrile 20:80 v/v; flux 1 ml/min, 1=220, 320 nm; $t_R$=8.4 min. 2) Column: BondClone 10, 10 mm, $C_{18}$, 3.9×300 mm, mobile phase: water/acetonitrile 20:80 v/v, flux=1 ml/min, 1=205, 245 nm); $t_R$=9.6 min.

$^1H$ NMR (200 MHz) ($CDCl_3$): d 0.07 (6H, s), 0.87 (9H, s), 1.23 (3H, d, J=6.2 Hz), 3.73 (1H, dd, J=1.6, 4.3 Hz), 4.60–4.81 (2H, m), 4.62 and 4.94 (2H, ABq, J=14 Hz), 5.20–5.47 (2H, m), 5.63 (1H, d, J=1.6 Hz), 5.81–6.03 (1H, m). $^{13}C$ NMR (50 MHz) ($CDCl_3$) : d −5.3, −4.7, 17.9, 22.3, 25.6, 37.6 ($CH_2$-Cl), 62.4, 64.9, 65.9, 72.0, 118.6, 121.8, 131.2, 150.9, 158.9, 172.3. MS EI: (m/z) 417 (M+).

EXAMPLE 4

To a solution of 19 g (0.056 moles) of (3S,4R)-3-[(R)-tert-butyldimethyl-silyloxy)-ethyl]-4-(2-chloroacetylthio)-2-azetidone in anhydrous toluene (150 ml) 14.1 ml (0.113 moles) of allyloxyoxalyl chloride are added under nitrogen at 0°–3° C. The solution is stirred for some minutes and then a solution of 11.7 ml (0.084 moles) triethylamine in toluene (10 ml) is added drop by drop. The solution is stirred for 90 minutes at the same temperature. 3.9 ml (0.028 moles) triethylamine are added, the solution stirred 90 minutes and filtered. The filtrate is washed with a cold aqueous solution of $NaHCO_3$ 5%, with water and with a solution of NaCl 10%; thereafter the solution is dried on anhydrous $Na_2SO_4$ and filtered. 20.4 g (0.123 moles) of triethyl-phosphite are added and the mixture is refluxed for 3 h.

The solution is cooled, concentrated under vacuum and purified by column chromatography (silica gel; cyclohexane/ethyl acetate 3:1 v/v), giving the desired allyl (5R,6S)-2-chloromethyl-6-((R)-1-tert-butyldimethylsilyloxy-ethyl)-penem-3-carboxylate as a yellow oil. Yield: 71%.

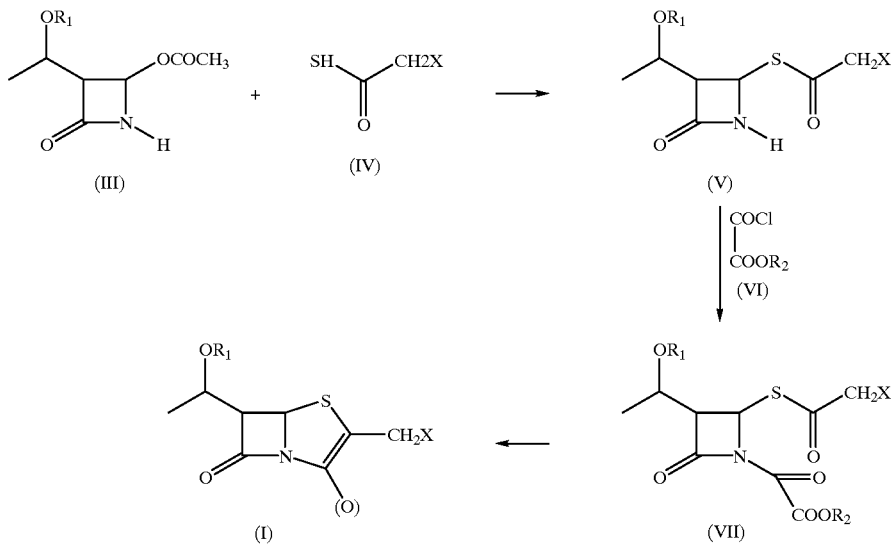

What is claimed is:

1. Process for the preparation of 2-halomethyl penems of formula (I)

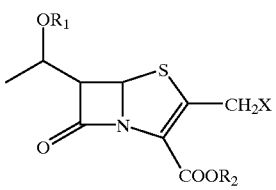

wherein $R_1$ is an hydroxy-protecting group, $R_2$ is a carboxyl-protecting group and X is halogen, wherein:

a) compounds of formula (III)

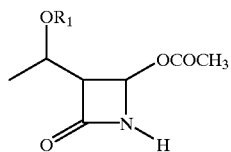

wherein $R_1$ is as above defined, are reacted with a 2-halothioacetic acid in an organic solvent in the presence of an organic base and a Lewis acid, at a temperature of $-10°$ C.$-+40°$ C., to give compounds of formula (V)

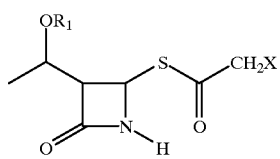

wherein $R_1$ and X are as above defined;

b) the above said compounds of formula (V) are reacted with an oxallyl chloride ester in an organic solvent in the presence of an organic base at a temperature of $-60°-+20°$ C., to give the compounds of formula (VII)

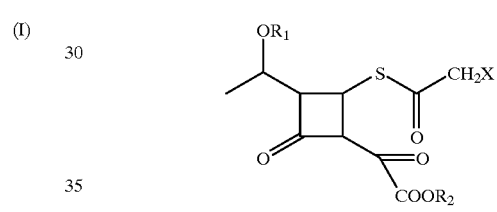

wherein $R_1$, $R_2$ and X are as above defined; and c) the compounds of formula (VII) are finally cyclized in an appropriate solvent at $20°–140°$ C. for 1–120 h, under the action of an organic phosphite or phosphonite.

2. Compounds of formula (VII)

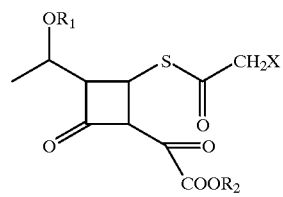

wherein $R_1$ is a hydroxy-protecting group selected from tertbutyl-dimethyl-silyl, trimethylsilyl, allyloxycarbonyl, p-nitrobenzyloxy-carbonyl, $R_2$ is a carboxyl-protecting group selected from allyl, benzyl (possibly substituted with a methoxy- or nitro-group), $CH_2OCO(O)_MR_4$ wherein $R_4$ is a $C_{1-6}$alkyl-group and m is 0 or 1 and X is halogen.

3. Process according to claim 1, for the preparation of derivatives of formula (I) wherein the protecting group $R_1$ is selected from the group consisting of: tertbutyl-dimethyl-silyl, trimethylsilyl, allyloxycarbonyl, p-nitrobenzyloxy-carbonyl; and the group $R_2$ is selected from the group consisting of: allyl, benzyl (possibly substituted with a methoxy- or nitro-group), $CH_2OCO(O)_MR_4$ wherein $R_4$ is a $C_{1-6}$alkyl-group and m is 0 or 1; the organic base is triethylamine or diisopropylethylamine, the Lewis acid is selected from the group consisting of: zinc iodide, zinc bromide, zinc chloride, aluminium chloride and the organic phosphite or phosphinite is a trimethyl-, triethyl-phosphite or a dimethoxymethylphosphine.

4. Process according to claim 1 wherein the 2-halothioacetic acid is the 2-chlorothioacetic acid.

5. Process according to claim 3 wherein the compound (I) obtained is a compound of formula (I)

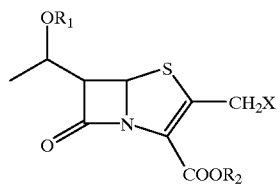

(I)

wherein: $R_1$ is tert-butyldimethylsilyl, $R_2$ is allyl, and X is Cl.

6. Compounds of formula (V)

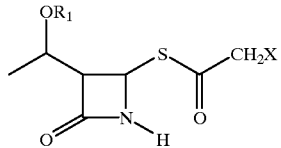

(V)

wherein $R_1$ is a hydroxy-protecting group selected from tertbutyl-dimethyl-silyl, trimethylsilyl, allyloxycarbonyl, p-nitrobenzyloxy-carbonyl and X is a halogen.

7. Compounds according to claim 2 wherein X is chlorine.

8. Compounds according to claim 6 wherein X is chlorine.

* * * * *